(12) United States Patent
Saito

(10) Patent No.: US 9,681,831 B2
(45) Date of Patent: Jun. 20, 2017

(54) ENDOSCOPE SYSTEM, ENDOSCOPE SYSTEM PROCESSOR DEVICE, OPERATION METHOD FOR ENDOSCOPE SYSTEM, AND OPERATION METHOD FOR ENDOSCOPE SYSTEM PROCESSOR DEVICE

(71) Applicant: FUJIFILM Corporation, Tokyo (JP)

(72) Inventor: Takaaki Saito, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 286 days.

(21) Appl. No.: 14/615,579

(22) Filed: Feb. 6, 2015

(65) Prior Publication Data

US 2015/0238127 A1 Aug. 27, 2015

(30) Foreign Application Priority Data

Feb. 27, 2014 (JP) .................................. 2014-037597

(51) Int. Cl.
*A61B 5/1455* (2006.01)
*A61B 5/1459* (2006.01)
(Continued)

(52) U.S. Cl.
CPC ........ *A61B 5/1459* (2013.01); *A61B 1/00009* (2013.01); *A61B 1/00055* (2013.01);
(Continued)

(58) Field of Classification Search
CPC .............. A61B 5/1455; A61B 5/14551; A61B 5/14552; A61B 5/0075; A61B 1/00009;
(Continued)

(56) References Cited

U.S. PATENT DOCUMENTS

2011/0273548 A1* 11/2011 Uchiyama .......... A61B 1/00009
348/68
2012/0116192 A1 5/2012 Saito
2013/0211217 A1 8/2013 Yamaguchi et al.

FOREIGN PATENT DOCUMENTS

| EP | 2522273 A1 | 11/2012 |
|---|---|---|
| JP | 5191329 B2 | 5/2013 |
| JP | 5231511 B2 | 7/2013 |

OTHER PUBLICATIONS

Extended European Search Report dated Jul. 24, 2015, for European Application No. 15152724.9.

\* cited by examiner

*Primary Examiner* — Eric Winakur
(74) *Attorney, Agent, or Firm* — Birch, Stewart, Kolasch & Birch, LLP

(57) ABSTRACT

The endoscope system includes: an image signal acquisition unit acquiring first image signal in first wavelength range where the amount of light absorption changes according to the concentration of yellow dye, second image signal in second wavelength range where the amount of light absorption changes according to the blood volume of an observation target, and third image signal in third wavelength range where a change in the amount of light absorption according to the concentration of the yellow dye is smaller than the first wavelength range and a change in the amount of light absorption according to the blood volume is smaller than the second wavelength range; a signal ratio calculation unit calculating first signal ratio based on the first and second image signals and calculating second signal ratio based on the second and third image signals; and a warning notification unit calculating a threshold value and generates warning signal.

20 Claims, 11 Drawing Sheets

(51) Int. Cl.
| | |
|---|---|
| *A61M 31/00* | (2006.01) |
| *A61B 1/04* | (2006.01) |
| *A61K 49/00* | (2006.01) |
| *A61B 1/00* | (2006.01) |
| *A61B 5/00* | (2006.01) |
| *A61B 1/06* | (2006.01) |
| *A61B 1/12* | (2006.01) |

(52) U.S. Cl.
CPC ............ *A61B 1/00057* (2013.01); *A61B 1/04* (2013.01); *A61B 1/0638* (2013.01); *A61B 1/0646* (2013.01); *A61B 1/126* (2013.01); *A61B 5/14552* (2013.01); *A61B 5/743* (2013.01); *A61K 49/006* (2013.01); *A61M 31/005* (2013.01)

(58) Field of Classification Search
CPC ........... A61B 1/04; A61B 1/06; A61B 5/7264; A61B 5/7271; A61B 5/7278
See application file for complete search history.

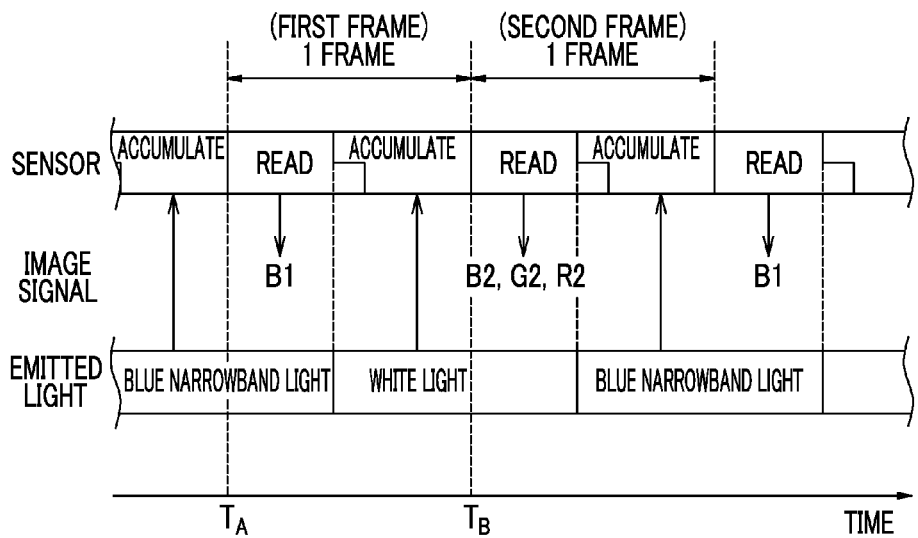
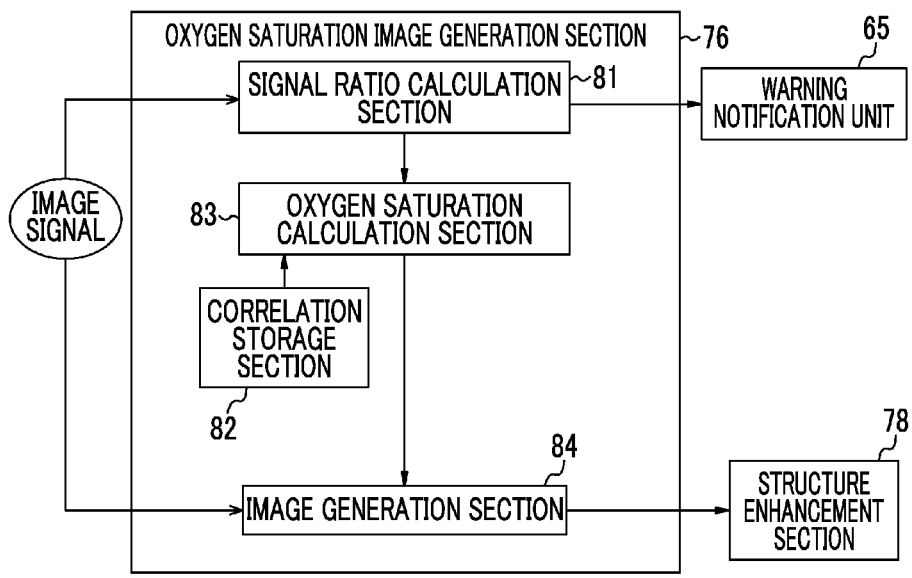

ENDOSCOPE SYSTEM, ENDOSCOPE SYSTEM PROCESSOR DEVICE, OPERATION METHOD FOR ENDOSCOPE SYSTEM, AND OPERATION METHOD FOR ENDOSCOPE SYSTEM PROCESSOR DEVICE

CROSS-REFERENCE TO RELATED APPLICATIONS

The present application claims priority under 35 U.S.C. §119 to Japanese Patent Application No. 2014-037597, filed on Feb. 27, 2014, all of which are hereby expressly incorporated by reference into the present application.

BACKGROUND OF THE INVENTION

1. Field of the Invention

The present invention relates to an endoscope system that images an observation target in a subject, an endoscope system processor device, an operation method for an endoscope system, and an operation method for an endoscope system processor device.

2. Description of the Related Art

In the medical field, it is common to perform diagnosis using an endoscope system including a light source device, an endoscope, and a processor device. In particular, an endoscope system has become widespread that acquires an observation image, in which a specific tissue or structure such as a blood vessel or a ductal structure is emphasized, not only simply by imaging an observation target but also by finding the wavelength of illumination light to be emitted to the observation target or by performing signal processing, such as spectral estimation processing, on an image signal obtained by imaging the observation target.

In such an endoscope system, when the observation target is contaminated (due to adhesion of residue or colored mucus, for example) or when dye for coloring is used, a target specific tissue may not be appropriately emphasized, or dirt or the like may be emphasized, for example. Therefore, for example, in an endoscope system for highlighting the blood vessels disclosed in JP5191329B, dye contained in residue or the like is detected based on a spectral estimation image, and an image is generated by correcting the influence of the dye. In recent years, there has also been an endoscope system that acquires biological function information based on an image signal obtained by imaging the observation target. For example, diagnosis of a lesion using the oxygen saturation of blood hemoglobin has been performed. As a method of acquiring the oxygen saturation, a method is known in which first signal light and second signal light having different wavelength bands and different absorption coefficients for oxygenated hemoglobin and reduced hemoglobin are alternately emitted to blood vessels in the mucous membrane and reflected light beams of the first and second signal light beams are detected by a sensor located at the distal end of the endoscope (refer to JP5231511B).

The ratio of signal values (hereinafter, referred to as a signal ratio) of pixels of an image signal corresponding to the reflected light of the first signal light detected by the sensor and an image signal corresponding to the reflected light of the second signal light detected by the sensor is maintained as a fixed value if there is no change in the oxygen saturation in the blood vessel. However, if there is a change in the oxygen saturation, the signal ratio is also changed accordingly. Therefore, it is possible to calculate the oxygen saturation based on the signal ratio of the image signals.

SUMMARY OF THE INVENTION

Since the oxygen saturation is calculated based on the signal ratio as described above, the calculation accuracy is reduced if the observation target is contaminated with dirt or the like that affects the signal ratio. For example, when the observation target is a mucous membrane of the lower digestive tract, mucus containing yellow (or yellow brown) dye, such as bilirubin or stercobilin, may adhere to the mucous membrane. The yellow dye absorbs light in a blue wavelength band. Accordingly, when the light in the blue wavelength band is used as signal light as disclosed in JP5191329B, signal light is absorbed not only by blood hemoglobin but also by the yellow dye. As a result, the oxygen saturation calculation accuracy may be reduced.

Although the observation target is washed in advance, it is not uncommon that there is residue, and mucus containing colored dye may be newly secreted during observation. In addition, the degree of reduction in the oxygen saturation calculation accuracy also differs depending on the amount of adhesion of residue, colored mucus, and the like. Therefore, in order to accurately calculate the oxygen saturation, it is necessary to take into consideration not only the presence of residue, colored mucus, and the like but also the amount. However, it is difficult to determine whether or not the degree of contamination of the observation target is high enough as to require cleaning.

It is an object of the invention to provide an endoscope system capable of displaying a warning when it is necessary to remove dirt, such as colored mucus, adhering to an observation target, an endoscope system processor device, an operation method for an endoscope system, and an operation method for an endoscope system processor device.

An endoscope system of the invention includes: an image signal acquisition unit that acquires a first image signal corresponding to a first wavelength range where an amount of light absorption changes according to concentration of yellow dye, a second image signal corresponding to a second wavelength range where the amount of light absorption changes according to a blood volume of an observation target, and a third image signal corresponding to a third wavelength range where a change in the amount of light absorption according to the concentration of the yellow dye is small compared with the first wavelength range and a change in the amount of light absorption according to the blood volume is small compared with the second wavelength range; a signal ratio calculation unit that calculates a first signal ratio for each pixel based on the first and second image signals and calculates a second signal ratio for each pixel based on the second and third image signals; and a warning notification unit that calculates a threshold value for comparison with the first signal ratio according to the second signal ratio and generates a warning signal for giving a warning for prompting cleaning of the observation target based on a comparison result between the first signal ratio and the threshold value.

It is preferable that the first signal ratio is a ratio of a pixel value of the second image signal to a pixel value of the first image signal.

It is preferable that the second signal ratio is a ratio of a pixel value of the third image signal to a pixel value of the second image signal.

It is preferable that the image signal acquisition unit acquires a fourth image signal corresponding to a fourth wavelength range where the amount of light absorption changes according to oxygen saturation of blood hemoglobin. In addition, it is preferable to further include an oxygen saturation calculation unit that calculates the oxygen saturation of the observation target for each pixel based on at least the fourth image signal.

It is preferable that the signal ratio calculation unit calculates a third signal ratio for each pixel based on the second and fourth image signals and that the warning notification unit calculates the threshold value for comparison with the first signal ratio according to the second and third signal ratios.

It is preferable that the third signal ratio is a ratio of a pixel value of the fourth image signal to a pixel value of the second image signal.

It is preferable to further include: an image generation unit that generates an oxygen saturation image showing the oxygen saturation of the observation target; and a display image signal generation unit that generates a display image signal for displaying the oxygen saturation image on a display unit. It is preferable that the warning signal includes a comparison result between the signal ratio of each pixel and the threshold value and that the display image signal generation unit makes a display in a pixel where the third signal ratio is within a specific range set in advance and a display in a pixel where the third signal ratio is outside the specific range different from each other based on the warning signal.

It is preferable that the display image signal generation unit generates the oxygen saturation image in which a color difference signal of the pixel where the third signal ratio is within the specific range is set to zero and a color difference signal of the pixel where the third signal ratio is outside the specific range is set to a value corresponding to the oxygen saturation.

It is preferable that the first wavelength range includes an isosbestic point at which the amount of light absorption does not change according to the oxygen saturation of blood hemoglobin.

An endoscope system processor device of the invention includes: an image signal acquisition unit that acquires a first image signal corresponding to a first wavelength range where an amount of light absorption changes according to concentration of yellow dye, a second image signal corresponding to a second wavelength range where the amount of light absorption changes according to a blood volume of an observation target, and a third image signal corresponding to a third wavelength range where a change in the amount of light absorption according to the concentration of the yellow dye is small compared with the first wavelength range and a change in the amount of light absorption according to the blood volume is small compared with the second wavelength range; a signal ratio calculation unit that calculates a first signal ratio for each pixel based on the first and second image signals and calculates a second signal ratio for each pixel based on the second and third image signals; and a warning notification unit that calculates a threshold value for comparison with the first signal ratio according to the second signal ratio and generates a warning signal for giving a warning for prompting cleaning of the observation target based on a comparison result between the first signal ratio and the threshold value.

An operation method for an endoscope system of the invention includes: a step of acquiring a first image signal corresponding to a first wavelength range where an amount of light absorption changes according to concentration of yellow dye, a second image signal corresponding to a second wavelength range where the amount of light absorption changes according to a blood volume of an observation target, and a third image signal corresponding to a third wavelength range where a change in the amount of light absorption according to the concentration of the yellow dye is small compared with the first wavelength range and a change in the amount of light absorption according to the blood volume is small compared with the second wavelength range using an image signal acquisition unit; a step of calculating a first signal ratio for each pixel based on the first and second image signals and calculating a second signal ratio for each pixel based on the second and third image signals using a signal ratio calculation unit; and a step of calculating a threshold value for comparison with the first signal ratio according to the second signal ratio and generating a warning signal for giving a warning for prompting cleaning of the observation target based on a comparison result between the first signal ratio and the threshold value using a warning notification unit.

An operation method for an endoscope system processor device of the invention includes: a step of acquiring a first image signal corresponding to a first wavelength range where an amount of light absorption changes according to concentration of yellow dye, a second image signal corresponding to a second wavelength range where the amount of light absorption changes according to a blood volume of an observation target, and a third image signal corresponding to a third wavelength range where a change in the amount of light absorption according to the concentration of the yellow dye is small compared with the first wavelength range and a change in the amount of light absorption according to the blood volume is small compared with the second wavelength range using an image signal acquisition unit; a step of calculating a first signal ratio for each pixel based on the first and second image signals and calculating a second signal ratio for each pixel based on the second and third image signals using a signal ratio calculation unit; and a step of calculating a threshold value for comparison with the first signal ratio according to the second signal ratio and generating a warning signal for giving a warning for prompting cleaning of the observation target based on a comparison result between the first signal ratio and the threshold value using a warning notification unit.

According to the endoscope system, the endoscope system processor device, the operation method for an endoscope system, and the operation method for an endoscope system processor device, it is possible to display a warning when it is necessary to remove dirt, such as colored mucus, adhering to an observation target.

BRIEF DESCRIPTION OF THE DRAWINGS

FIG. 7 is an explanatory diagram showing imaging control in the special observation mode.
FIG. 8 is a block diagram of an oxygen saturation image generation section and a diagnostic information calculation unit.

DESCRIPTION OF THE PREFERRED EMBODIMENTS

First Embodiment

Figure 1:
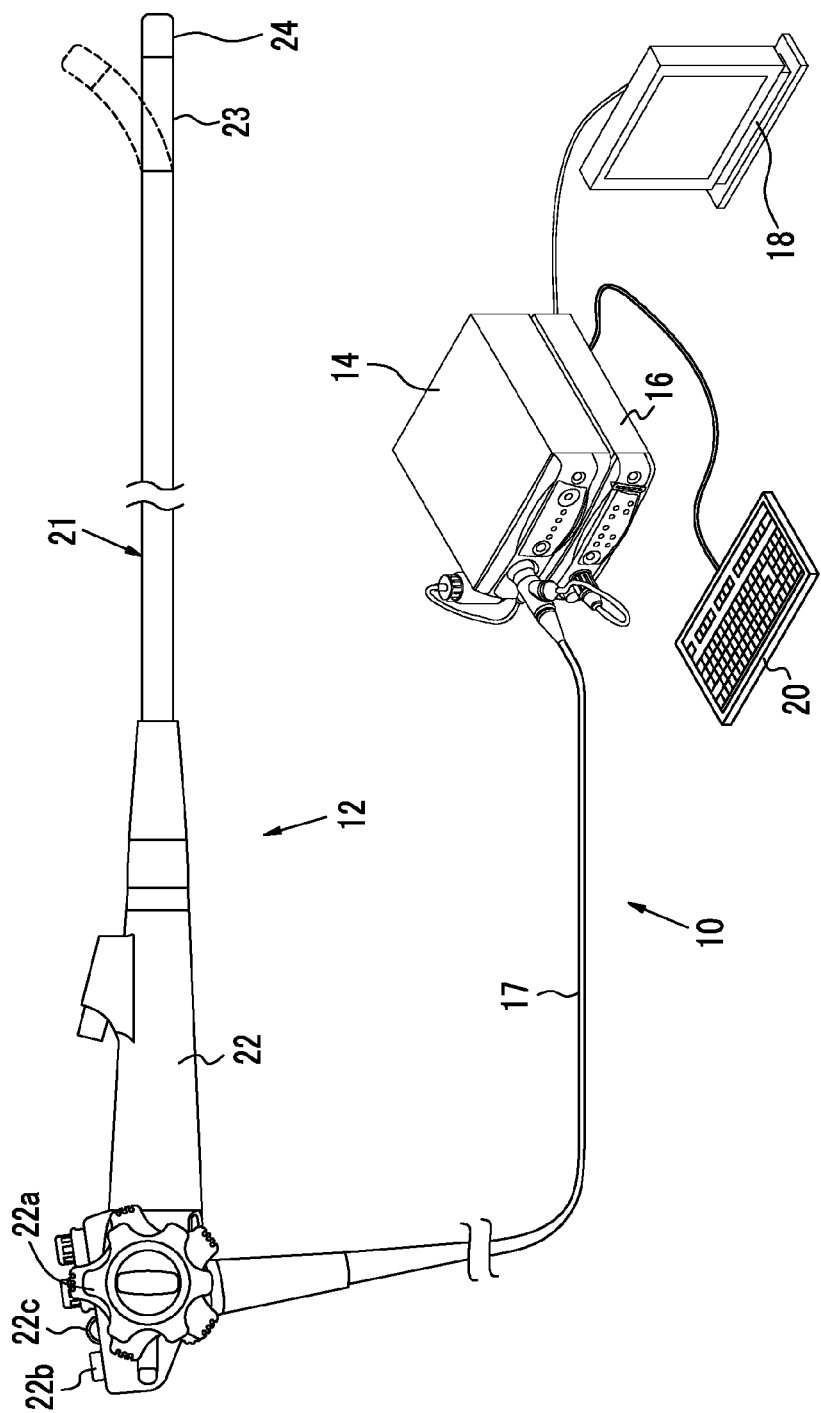
FIG. 1 is an external view of an endoscope system.

As shown in FIG. 1, an endoscope system 10 according to a first embodiment includes an endoscope 12, a light source device 14, a processor device 16, a monitor 18 (display unit), and a console 20. The endoscope 12 is optically connected to the light source device 14, and is electrically connected to the processor device 16. The endoscope 12 includes an insertion unit 21 that is inserted into a subject, an operating unit 22 provided at the base end of the insertion unit 21, and a bending portion 23 and a distal portion 24 that are provided at the distal side of the insertion unit 21. By operating an angle knob 22a of the operating unit 22, the bending portion 23 is bent. The distal portion 24 can be directed in a desired direction by the bending operation.

In addition to the angle knob 22a, an observation mode selector SW (observation mode selector switch) 22b, a zoom operation portion 22c, and a freeze button (not shown) for saving a still image are provided in the operating unit 22. The mode selector SW 22b is used for a switching operation between two modes of the normal observation mode and the special observation mode. The normal observation mode is a mode in which a normal light image obtained by full-color imaging of the observation target in the subject is displayed on the monitor 18. The special observation mode is a mode in which an oxygen saturation image obtained by imaging the oxygen saturation of blood hemoglobin of the observation target is displayed on the monitor 18. The zoom operation portion 22c is used for a zooming operation for driving a zoom lens 47 (refer to FIG. 2) in the endoscope 12 to magnify the observation target.

The processor device 16 is electrically connected to the monitor 18 and the console 20. The monitor 18 displays an image, such as a normal light image or an oxygen saturation image, and information regarding the image (hereinafter, referred to as image information or the like). The console 20 functions as a user interface (UI) for receiving an input operation, such as a function setting. A recording unit (not shown) in which image information or the like is recorded may be connected to the processor device 16.

Figure 2:
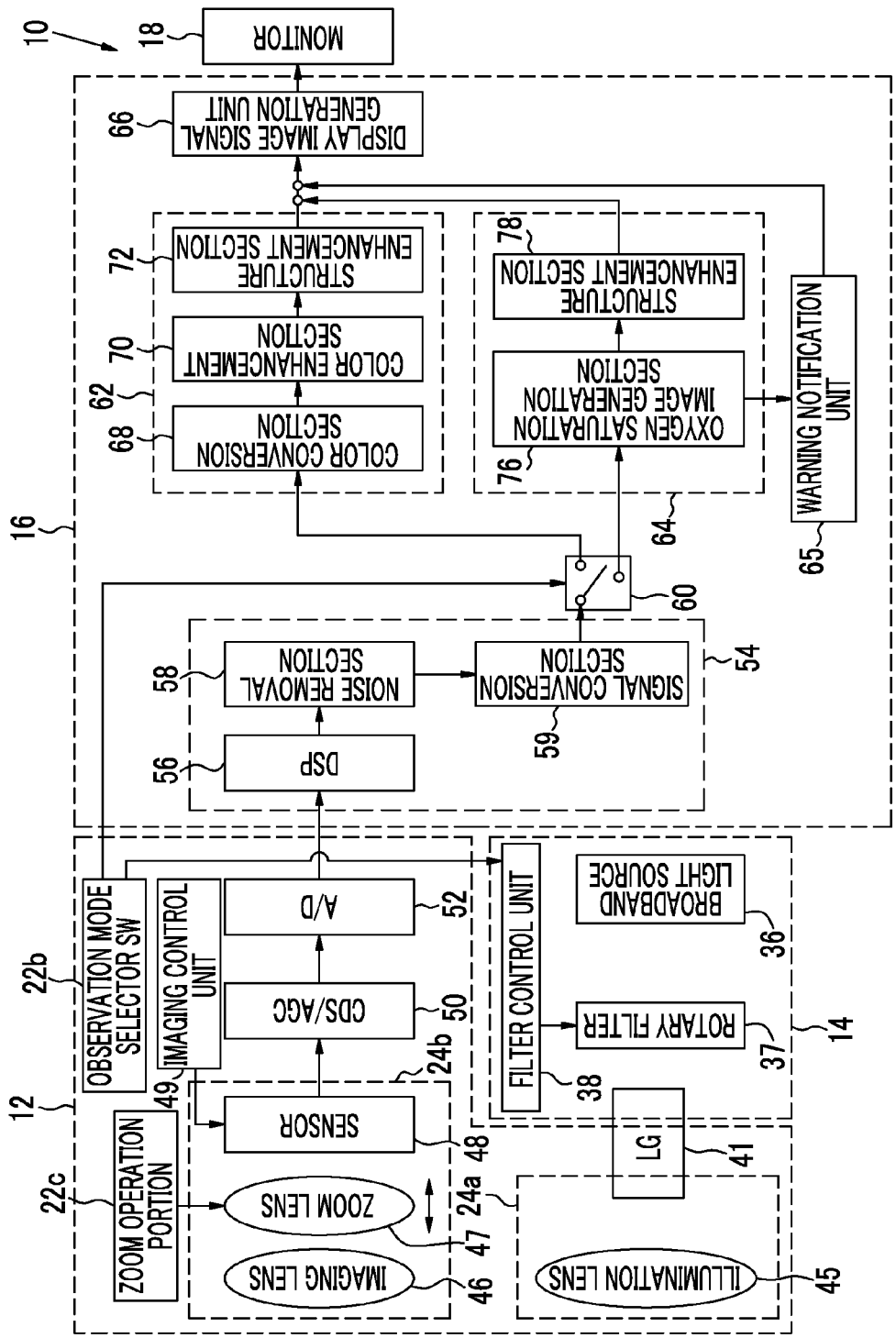
FIG. 2 is a block diagram of the endoscope system.
Figure 3:
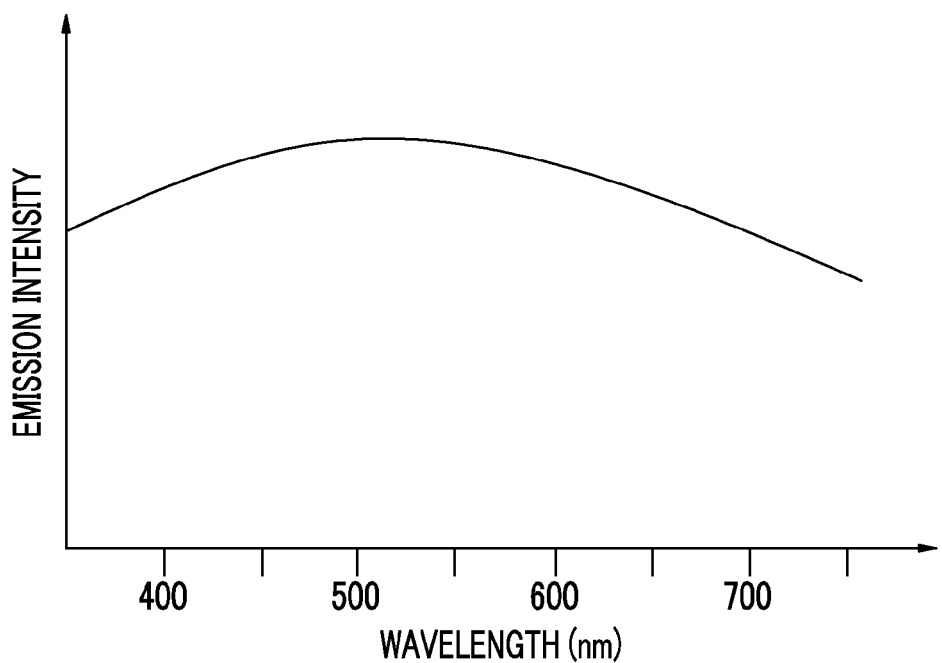
FIG. 3 is a graph showing the spectrum of white light.

As shown in FIG. 2, the light source device 14 includes a broadband light source 36, a rotary filter 37, and a filter control unit 38. The broadband light source 36 is, for example, a xenon lamp or a white light emitting diode (LED), and emits white light in a wavelength band ranging from blue to red as shown in FIG. 3. The white light emitted from the broadband light source 36 is incident on a light guide (LG) 41 through optical members, such as a condensing lens, an optical fiber, and a multiplexer (none are shown) or the rotary filter 37. The light guide 41 is built into a universal cord 17 that connects the endoscope 12 and the light source device 14 to each other (refer to FIG. 1) and the endoscope 12. The light guide 41 causes the incident light to propagate to the distal portion 24 of the endoscope 12. As the light guide 41, a multi-mode fiber can be used. As an example, it is possible to use a small-diameter fiber cable having a diameter of $\phi 0.3$ mm to $\phi 0.5$ mm that includes a core with a diameter of 105 μm, a cladding with a diameter of 125 μm, and a protective layer as an outer skin.

Figure 4:
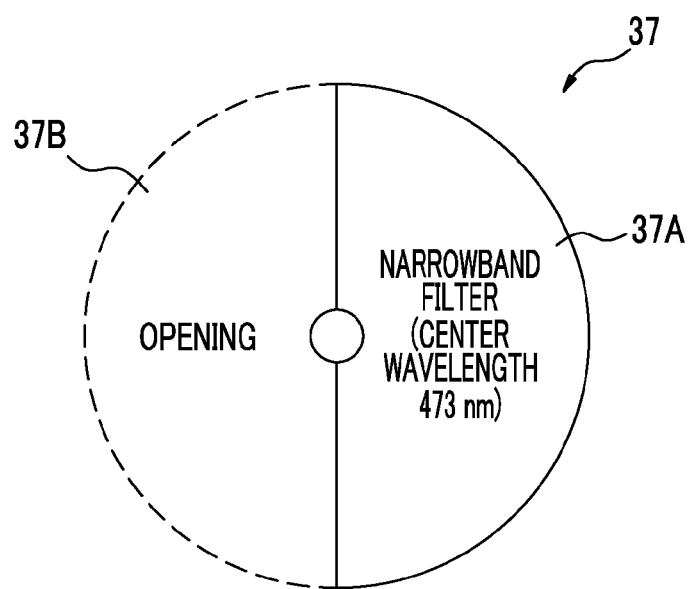
FIG. 4 is an explanatory diagram of a rotary filter.

The rotary filter 37 is rotatably disposed on the optical path along which the white light generated by the broadband light source 36 is incident on the light guide 41. As shown in FIG. 4, the rotary filter 37 includes a narrowband filter 37A and an opening 37B. The narrowband filter 37A limits the wavelength band of light to be transmitted therethrough to light having a center wavelength of 473±10 nm (hereinafter, referred to as blue narrowband light) that is a wavelength band where the amount of light absorption changes according to the oxygen saturation of blood hemoglobin, and cuts light having a wavelength in other wavelength bands. Therefore, when the narrowband filter 37A is disposed on the optical path, only the blue narrowband light of the white light emitted from the broadband light source 36 is transmitted through the narrowband filter 37A and is then incident on the light guide 41. In this case, illumination light emitted to the observation target is the blue narrowband light. On the other hand, when the opening 37B is disposed on the optical path, the white light emitted from the broadband light source 36 is incident on the light guide 41 as it is. In this case, illumination light emitted to the observation target is the white light.

The filter control unit 38 controls the rotation of the rotary filter 37. In the special observation mode, the filter control unit 38 rotates the rotary filter 37 in synchronization with the imaging timing of the observation target. Accordingly, the narrowband filter 37A and the opening 37B alternately pass through the optical path of the white light emitted from the broadband light source 36, and the blue narrowband light and the white light are alternately emitted to the observation target. On the other hand, in the normal observation mode, the filter control unit 38 stops the rotation of the rotary filter 37 in a state where the opening 37B is disposed on the optical path of the white light emitted from the broadband light source 36. As a result, in the normal observation mode, the white light is emitted to the observation target.

The broadband light source 36 and the rotary filter 37 form a light source that generates illumination light to irradiate the observation target. In the present embodiment, the filter control unit 38 controls the rotation and stop of the rotary filter 37 as described above. However, when the rotary filter 37 is provided so as to be retractable from the optical path of the white light, the filter control unit 38 may retract the rotary filter 37 in the normal observation mode, so that the white light is directly incident on the light guide 41 without passing through the rotary filter 37.

The distal portion 24 of the endoscope 12 includes an illumination optical system 24a and an imaging optical system 24b. An illumination lens 45 is provided in the illumination optical system 24a, and the white light or the blue narrowband light from the light guide 41 is emitted to the observation target through the illumination lens 45.

The imaging optical system 24b of the endoscope 12 includes an imaging lens 46, the zoom lens 47, and a sensor 48 (refer to FIG. 2). Reflected light from the observation target is incident on the sensor 48 through the imaging lens 46 and the zoom lens 47. Then, a reflected image of the observation target is formed on the sensor 48. The zoom lens 47 is moved between the tele end and the wide end by operating the zoom operation portion 22c. When the zoom lens 47 is moved to the tele end side, the reflected image of the observation target is magnified. On the other hand, when the zoom lens 47 is moved to the wide end side, the reflected image of the observation target is reduced. When magnified observation is not performed (at the time of non-magnified observation), the zoom lens 47 is disposed at the wide end. When performing magnified observation, the zoom lens 47 is moved from the wide end to the tele end side by operating the zoom operation portion 22c.

The sensor 48 is a color imaging device, and captures a reflected image of the observation target and outputs the image signal. As the sensor 48, for example, a charge coupled device (CCD) image sensor or a complementary metal oxide semiconductor (CMOS) image sensor can be used. In the present embodiment, the sensor 48 is a CCD image sensor. The sensor 48 includes RGB pixels in which RGB color filters are provided on the imaging surface, and outputs image signals of three colors of R, G, and B by performing photoelectric conversion in pixels of respective colors of RGB.

Figure 5:
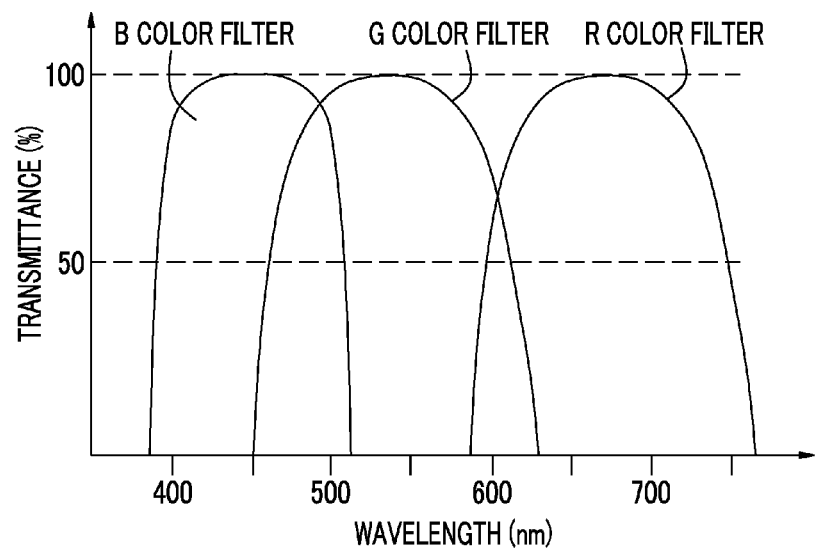
FIG. 5 is a graph showing the spectral transmittance of an RGB color filter.

As shown in FIG. 5, the B color filter has a spectral transmittance of 390 nm to 510 nm, and the center wavelength of the wavelength band of light transmitted through the B color filter is set to 450 nm in the present embodiment. The center wavelength of the B color filter is preferably set such that the difference between the center wavelength of the B color filter and the center wavelength of the wavelength band (473±10 nm) of the blue narrowband light is 20 nm or more and 100 nm or less. The G color filter has a spectral transmittance of 450 nm to 630 nm, and the R color filter has a spectral transmittance of 580 nm to 760 nm. Accordingly, the G color filter transmits light in a wavelength band where the amount of light absorption changes according to the blood volume of the observation target, and the R color filter transmits light in a wavelength band where a change in the amount of light absorption according to the oxygen saturation and the blood volume is smaller than that for the B color filter or the G color filter.

The sensor 48 includes color filters having the characteristics described above. Therefore, when the blue narrowband light is emitted to the observation target as illumination light, an image signal corresponding to the reflected light of the blue narrowband light is obtained from at least the B pixel. On the other hand, when the white light is emitted to the observation target, an image signal corresponding to the color filter of each color is obtained from each of RGB pixels.

As the sensor 48, it is also possible to use a so-called complementary color image sensor including complementary color filters of C (cyan), M (magenta), Y (yellow), and G (green) on the imaging surface. When using the complementary color image sensor as the sensor 48, a color converter that performs color conversion from image signals of four colors of CMYG to image signals of three colors of RGB is preferably provided in the endoscope 12, the light source device 14, or the processor device 16. In this manner, even when complementary color image sensors are used, it is possible to obtain the image signals of three colors of RGB from the image signals of four colors of CMYG by color conversion.

Figure 6:
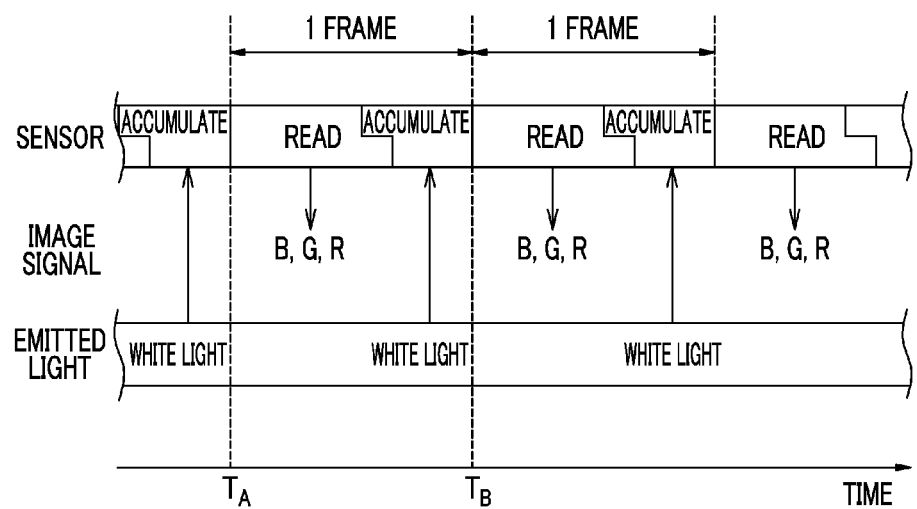
FIG. 6 is an explanatory diagram showing imaging control in the normal observation mode.

An imaging control unit 49 performs imaging control of the sensor 48. As shown in FIG. 6, in the normal observation mode, an observation target illuminated by white light is imaged by the sensor 48 every period of one frame (hereinafter, simply referred to as one frame). Then, the image signals of RGB are output from the sensor 48 for each frame. In the present embodiment, the sensor 48 is a CCD image sensor. Accordingly, one frame is a period of the length from the end (time $T_A$) of a charge accumulation period (also referred to as an exposure period) to the end of the next charge accumulation period (time $T_B$), for example. In addition, since the sensor 48 is a CCD image sensor, one frame is divided into a reading period and a charge accumulation period in FIG. 6. However, the approximately entire one frame can be set as a charge accumulation period, and signal charges accumulated in the previous frame can also be read during the accumulation of signal charges. The imaging control unit 49 also performs control, such as the adjustment of the length of the charge accumulation period.

Also in the special observation mode, the imaging control unit 49 performs imaging control of the sensor 48 in the same manner as in the normal observation mode. However, in the special observation mode, the blue narrowband light and the white light are alternately emitted to the observation target in synchronization with the imaging frame of the sensor 48. Therefore, as shown in FIG. 7, the sensor 48 reads signal charges, which are obtained by imaging the observation target under the blue narrowband light, in the reading period of the first frame, and outputs the image signal from at least the B pixel. Then, the sensor 48 reads signal charges, which are obtained by imaging the observation target under the white light, in the reading period of the second frame, and outputs the image signals of RGB colors. The sensor 48 outputs the image signals of RGB colors in both the first and second frames. However, the spectrum of illumination light in the first frame and the spectrum of illumination light in the second frame are different. Therefore, for the sake of distinction, an image signal that the sensor 48 outputs from the B pixel in the first frame is referred to as a B1 image signal. Although not used in the present embodiment, image signals output from the R and G pixels in the first frame are referred to as an R1 image signal and a G1 image signal, respectively. Image signals of RGB colors output in the second frame are referred to as an R2 image signal, a G2 image signal, and a B2 image signal, respectively.

The B1 image signal is an image signal corresponding to the wavelength band of the blue narrowband light where the amount of light absorption changes according to the oxygen saturation of blood hemoglobin. The B2 image signal is an image signal corresponding to the wavelength band of the B color filter. In the wavelength band of the B color filter, the amount of light absorption mainly changes according to the concentration of yellow dye. Accordingly, the B2 image signal is an image signal having a signal value corresponding to the concentration of the yellow dye. The G2 image signal is an image signal corresponding to the wavelength band of the G color filter. In the wavelength band of the G color filter, the amount of light absorption mainly changes according to the blood volume of the observation target. Accordingly, the G2 image signal is an image signal having a signal value corresponding to the blood volume of the observation target. The R2 image signal is an image signal corresponding to the wavelength band of the R color filter. In the wavelength band of the R color filter, a change in the amount of light absorption due to yellow dye, oxygen saturation, and blood volume is smaller than that in the B color filter and the G color filter. Accordingly, the R2 image signal is an image signal having a signal value with lower dependence on the yellow dye, the oxygen saturation, and the blood volume than the B2 image signal and the G2 image signal. In the present embodiment, when calculating the oxygen saturation, the G2 image signal is used as an image signal to be a reference of the B1 image signal or the R2 image signal, and is accordingly used for standardization of the B1 image signal or the R2 image signal. However, other image signals may also be used for standardization.

In order to calculate the oxygen saturation, a signal ratio B1/G2 between the B1 image signal and the G2 image signal and a signal ratio R2/G2 between the R2 image signal and the G2 image signal are used. Among these signal ratios, the signal ratio B1/G2 between the B1 image signal and the G2 image signal using the B1 image signal corresponding to the wavelength band of the blue narrowband light is a signal ratio that is required for the calculation of the oxygen saturation. For this reason, the blue narrowband light is first signal light for calculating the oxygen saturation, and a component (component transmitted through the G color filter) that becomes the G2 image signal in the white light is second signal light for calculating the oxygen saturation.

The image signals of the respective colors output from the sensor 48 are transmitted to a correlated double sampling (CDS)/automatic gain control (AGC) circuit 50 (refer to FIG. 2). The CDS/AGC circuit 50 performs correlated double sampling (CDS) or automatic gain control (AGC) for the analog image signals output from the sensor 48. The image signals transmitted through the CDS/AGC circuit 50 are converted into digital image signals by an A/D converter 52. The image signals that have been digitized in this manner are input to the processor device 16.

The processor device 16 includes an image signal acquisition unit 54, an image processing switching unit 60, a normal observation image processing unit 62, a special observation image processing unit 64, a warning notification unit 65, and a display image signal generation unit 66. The image signal acquisition unit 54 receives an image signal input from the endoscope 12. The image signal acquisition unit 54 includes a digital signal processor (DSP) 56, a noise removal section 58, and a signal conversion section 59.

The DSP 56 performs various kinds of signal processing, such as defect correction processing, offset processing, gain correction processing, linear matrix processing, gamma conversion processing, demosaic processing, and YC conversion processing, on the received image signal. By the defect correction processing, the signal of the defective pixel of the sensor 48 is corrected. By the offset processing, a dark current component is removed from the image signal subjected to the defect correction processing, and the accurate zero level is set. In the gain correction processing, the signal level of each image signal is adjusted by multiplying each of the RGB image signals after the offset processing by a specific gain. Linear matrix processing for increasing color reproducibility is performed on the image signal of each color after the gain correction processing. Then, the brightness or saturation of each image signal is adjusted by gamma conversion processing. Demosaic processing (also referred to as isotropic processing or synchronization processing) is performed on the image signal after the linear matrix processing, and the missing color signal of each pixel is generated by interpolation. Through the demosaic processing, all pixels have signals of RGB colors. The DSP 56 performs YC conversion processing on each image signal after the demosaic processing, and outputs a brightness signal Y and color difference signals Cb and Cr to the noise removal section 58.

The noise removal section 58 performs noise removal processing using, for example, a moving average method or a median filter method on the image signal subjected to the demosaic processing or the like by the DSP 56. The image signals after noise has been removed are input to the signal conversion section 59, are reconverted into RGB image signals, and are input to the image processing switching unit 60.

When the observation mode selector SW 22b is set to the normal observation mode, the image processing switching unit 60 inputs the image signals to the normal observation image processing unit 62. On the other hand, when the observation mode selector SW22b is set to the special observation mode, the image processing switching unit 60 inputs the image signals to the special observation image processing unit 64.

The normal observation image processing unit 62 includes a color conversion section 68, a color enhancement section 70, and a structure enhancement section 72. The color conversion section 68 generates RGB image data by assigning the input RGB image signals of one frame to R, G and B pixels. Then, color conversion processing, such as 3×3 matrix processing, gradation conversion processing, and three-dimensional LUT processing, is performed on the RGB image data.

The color enhancement section 70 performs various kinds of color enhancement processing on the RGB image data after the color conversion processing. The structure enhancement section 72 performs structure enhancement processing, such as spatial frequency enhancement, on the RGB image data after the color enhancement processing. The RGB image data subjected to the structure enhancement processing by the structure enhancement section 72 is input to the display image signal generation unit 66 as a normal observation image.

The special observation image processing unit 64 includes an oxygen saturation image generation section 76 and a structure enhancement section 78. The oxygen saturation image generation section 76 calculates the oxygen saturation, and generates an oxygen saturation image indicating the calculated oxygen saturation.

The structure enhancement section 78 performs structure enhancement processing, such as spatial frequency enhancement processing, on the oxygen saturation image input from the oxygen saturation image generation section 76. The oxygen saturation image subjected to the structure enhancement processing by the structure enhancement section 72 is input to the display image signal generation unit 66.

The display image signal generation unit 66 converts the normal observation image or the oxygen saturation image into a display format signal (display image signal), and inputs the display format signal to the monitor 18. As a result, the normal observation image or the oxygen saturation image is displayed on the monitor 18.

As shown in FIG. 8, the oxygen saturation image generation section 76 includes a signal ratio calculation section 81, a correlation storage section 82, an oxygen saturation calculation section 83, and an image generation section 84.

The signal ratio calculation section 81 calculates a signal ratio that is used when the oxygen saturation calculation section 83 calculates the oxygen saturation and a signal ratio that is used in the warning notification unit 65. The signal ratio calculated by the signal ratio calculation section 81 is a ratio of signal values of two image signals for each pixel. Specifically, the signal ratio calculation section 81 calculates the signal ratio B1/G2 (third signal ratio) between the B1 image signal and the G2 image signal, the signal ratio R2/G2 (second signal ratio) between the R2 image signal and the G2 image signal, and the signal ratio G2/B2 (first signal ratio) between the G2 image signal and the B2 image signal for each pixel. The signal ratio B1/G2 and the signal ratio R2/G2 are used in the oxygen saturation calculation section 83 and the warning notification unit 65, and the signal ratio G2/B2 is used in the warning notification unit 65.

The correlation storage section 82 stores a correlation between each signal ratio calculated by the signal ratio calculation section 81 and the oxygen saturation. This correlation is stored in a two-dimensional table that defines the isolines of oxygen saturation on a two-dimensional space shown in FIG. 9, and the position and shape of each isoline for the signal ratio are obtained in advance by physical simulation of light scattering. The distance between isolines changes according to the signal ratio R2/G2 indicating the blood volume. In addition, the correlation between the signal ratio and the oxygen saturation is stored in a log scale.

Figure 10:
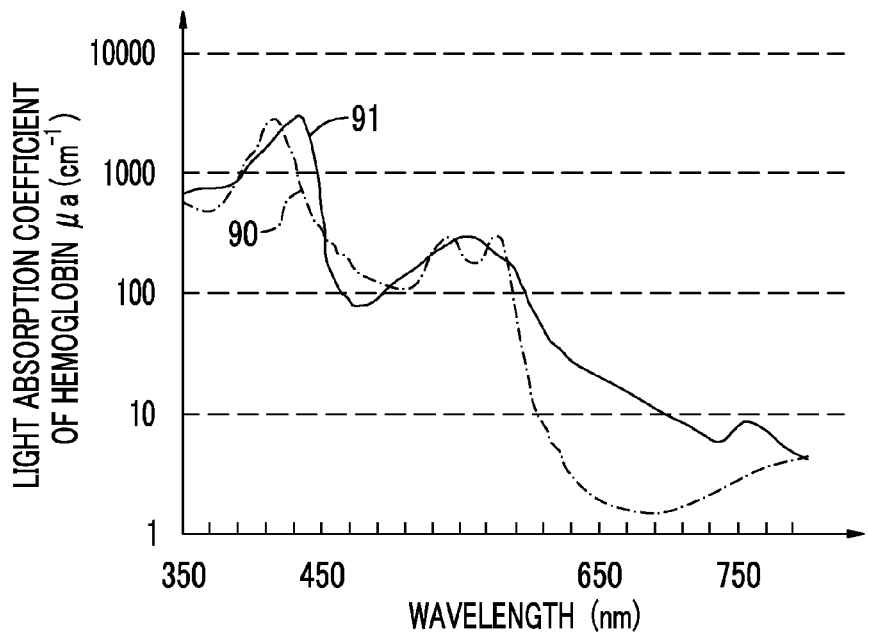
FIG. 10 is a graph showing the absorption coefficients of oxygenated hemoglobin and reduced hemoglobin.

The above correlation is closely related to the absorption characteristics or light scattering characteristics of oxygenated hemoglobin (graph 90) or reduced hemoglobin (graph 91) shown in FIG. 10. For example, as at a center wavelength of 473 nm of the blue narrowband light, at a wavelength at which the difference between the absorption coefficient of oxygenated hemoglobin and the absorption coefficient of reduced hemoglobin is large, it is easy to handle the information of the oxygen saturation. However, the B1 image signal corresponding to 473-nm light has a high dependence not only on the oxygen saturation but also on the blood volume. Therefore, by using the signal ratio R2/G2 obtained from the R2 image signal and the G2 image signal as well as the B1 image signal, it is possible to accurately calculate the oxygen saturation without there being dependency on the blood volume. Here, the G2 image signal corresponds to light that changes mainly depending on the blood volume, and the R2 image signal is a signal with low dependence on the yellow dye, the oxygen saturation, and the blood volume.

Figure 11:
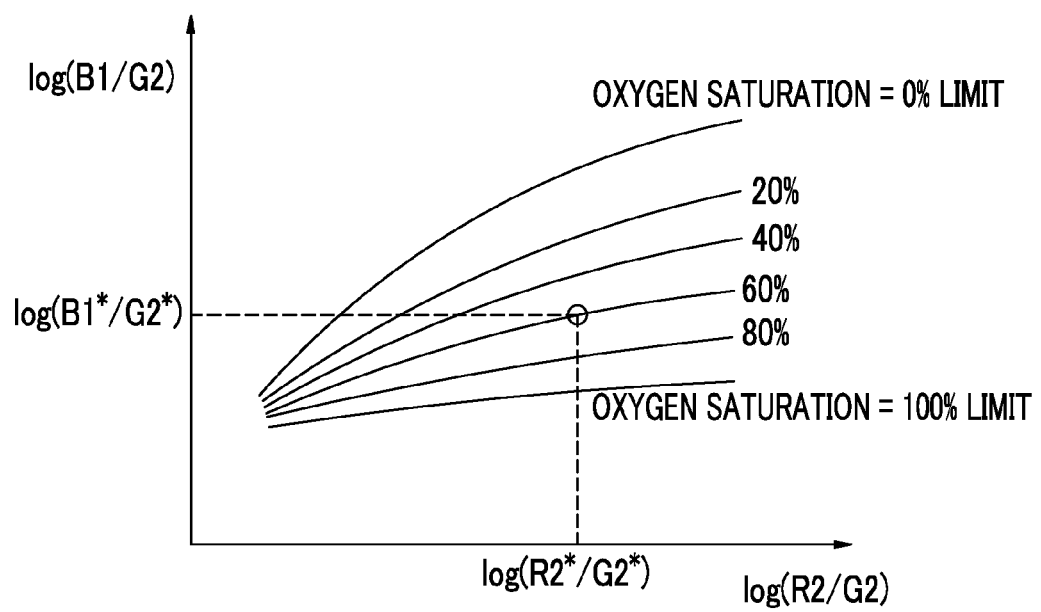
FIG. 11 is an explanatory diagram showing a method of calculating the oxygen saturation.

The oxygen saturation calculation section 83 calculates the oxygen saturation using the signal ratio B1/G2 and the signal ratio R2/G2 calculated by the signal ratio calculation section 81. More specifically, the oxygen saturation calculation section 83 calculates the oxygen saturation corresponding to the signal ratio calculated by the signal ratio calculation section 81, for each pixel, with reference to the correlation stored in the correlation storage section 82. For example, when the signal ratio B1/G2 and the signal ratio R2/G2 in a specific pixel are B1*/G2* and R2*/G2*, respectively, the oxygen saturation corresponding to the signal ratio B1*/G2*, the signal ratio R2*/G2*, and the signal ratio G2*/B2* is "60%" when the correlation shown in FIG. 11 is referred to. Accordingly, the oxygen saturation calculation section 83 calculates the oxygen saturation of the specified pixel as "60%".

In addition, a case where the signal ratio B1/G2 and the signal ratio R2/G2 become extremely large or extremely small hardly occurs. That is, a case hardly occurs in which a combination of the signal ratio B1/G2 and the signal ratio R2/G2 exceeds a lower limit isoline 93 (refer to FIG. 9) of the oxygen saturation of 0% or on the contrary becomes lower than an upper limit isoline 94 (refer to FIG. 9) of the oxygen saturation of 100%. Here, the oxygen saturation calculation section 83 sets the oxygen saturation to 0% when the calculated oxygen saturation is lower than the lower limit isoline 93, and sets the oxygen saturation to 100% when the calculated oxygen saturation exceeds the upper limit isoline 94. When a point corresponding to the signal ratio B1/G2, the signal ratio R2/G2, and/or the signal ratio G2/B2 deviates from a region between the lower limit isoline 93 and the upper limit isoline 94, display showing that the reliability of the oxygen saturation in the pixel is low may be performed, or the oxygen saturation may not be calculated.

The image generation section 84 generates an oxygen saturation image by imaging the oxygen saturation using the oxygen saturation calculated by the oxygen saturation calculation section 83. Specifically, the image generation section 84 acquires a B2 image signal, a G2 image signal, and an R2 image signal, and multiplies these image signals by the gain corresponding to the oxygen saturation for each pixel. Then, RGB image data is generated using the B2 image signal, the G2 image signal, and the R2 image signal multiplied by the gain. For example, in a pixel where the oxygen saturation is 60% or more, the image generation section 84 multiplies all of the B2 image signal, the G2 image signal, and the R2 image signal by the same gain "1". In contrast, in a pixel where the oxygen saturation is less than 60%, the image generation section 84 multiplies the B2 image signal by the gain of less than "1" and multiplies the G2 image signal and the R2 image signal by the gain of "1" or more. RGB image data generated using the B2 image signal, the G2 image signal, and the R2 image signal after the gain processing is the oxygen saturation image.

In the oxygen saturation image generated by the image generation section 84, a high oxygen region (region having an oxygen saturation of 60% to 100%) is expressed in the same color as the normal observation image. On the other hand, a low oxygen region where the oxygen saturation is less than a specific value (region having an oxygen saturation of 0% to 60%) is expressed in a different color (pseudo color) from the normal observation image.

Although the image generation section 84 performs gain multiplication for pseudo coloring only for the low oxygen region in the present embodiment, a gain corresponding to the oxygen saturation may also be multiplied for the high oxygen region so that the entire oxygen saturation image is pseudo-colored. In addition, although the low oxygen region and the high oxygen region are divided at the oxygen saturation of 60%, this boundary can be arbitrarily selected.

Figure 12:
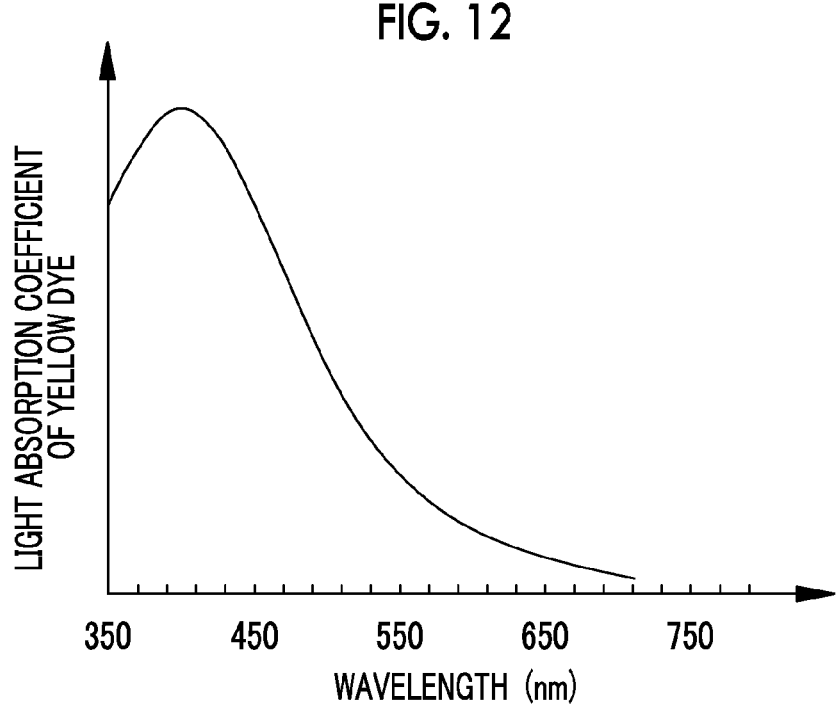
FIG. 12 is a graph showing the typical absorption coefficient spectrum of yellow dye.

The warning notification unit 65 acquires the signal ratio G2/B2 from the signal ratio calculation section 81, compares the signal ratio G2/B2 with a threshold value $Q_{TH}$, and generates a warning signal based on the comparison result. Specifically, when there is a pixel having the signal ratio G2/B2 equal to or greater than the threshold value $Q_{TH}$, a warning signal is generated. As shown in FIG. 12, yellow dye, such as bilirubin or stercobilin contained in mucus, residue, or the like has a spectrum that gradually decreases with respect to the wavelength. For this reason, if dirt, such as mucus containing yellow dye, adheres to the observation target, the signal value of the B2 image signal is smaller than that when there is no yellow dye due to light absorption by the yellow dye. Therefore, the value of the signal ratio G2/B2 increases.

Similarly, when mucus containing yellow dye or the like adheres to the observation target, the signal value of the B1 image signal is smaller than that when there is no yellow dye due to light absorption by the yellow dye. Therefore, the value of the signal ratio B1/G2 for calculating the oxygen saturation is reduced. Thus, if the observation target is contaminated with mucus containing yellow dye or the like, a problem occurs in which the oxygen saturation is measured as being high according to the amount or concentration of yellow dye.

Therefore, the signal ratio G2/B2 is a signal ratio as a measure of the presence or concentration (or total amount) of the yellow dye, and is a signal ratio as a measure of the error of oxygen saturation occurring due to the yellow dye. Using this, the warning notification unit 65 generates a warning signal when the signal ratio G2/B2 is large and the observation target is severely contaminated with mucus containing yellow dye or the like (when the error of the oxygen saturation is large). The warning signal is input to the display image signal generation unit 66.

Figure 13:
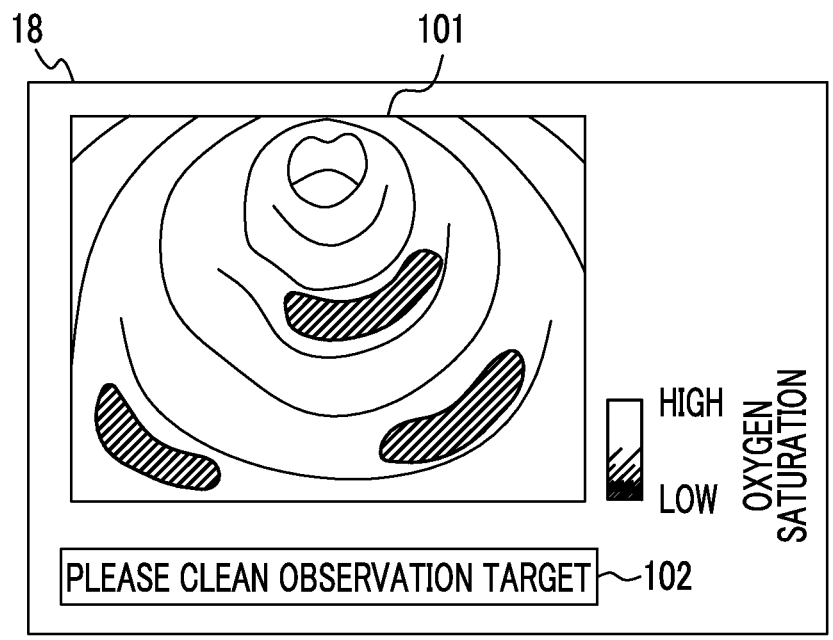
FIG. 13 is an explanatory view showing a manner of giving a warning.

As shown in FIG. 13, when the warning signal is input, the display image signal generation unit 66 displays a warning message 102 prompting the cleaning of the observation target on the monitor 18 together with an oxygen saturation image 101.

Figure 14:
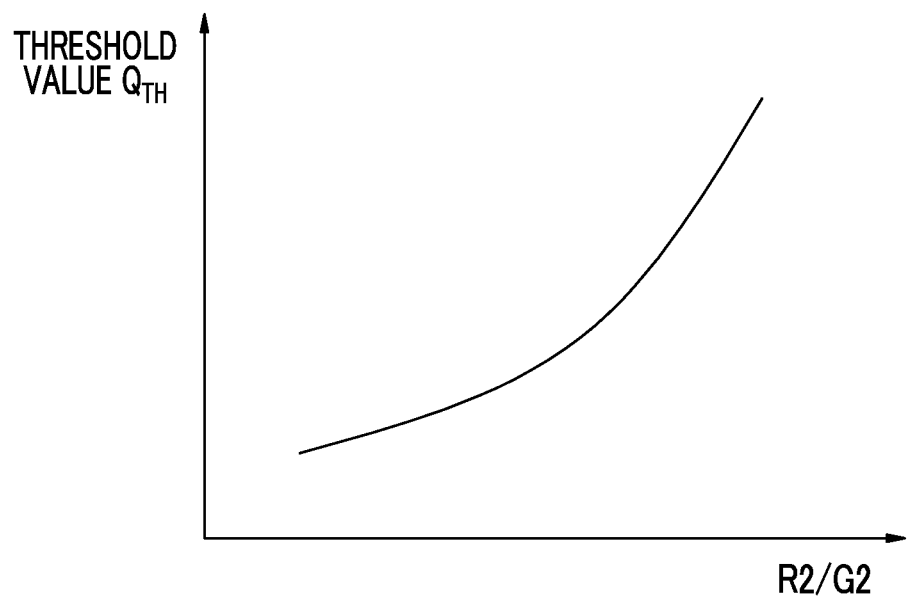
FIG. 14 is a graph showing the relationship between a threshold value and the signal ratio R2/G2.

The warning notification unit 65 acquires the signal ratio R2/G2 (second signal ratio) from the signal ratio calculation section 81, and changes the threshold value $Q_{TH}$ for comparison with the signal ratio G2/B2 (first signal ratio) according to the signal ratio R2/G2 (second signal ratio), for example, as shown in FIG. 14. That is, since the signal ratio R2/G2 mainly changes according to the blood volume, the warning notification unit 65 changes the threshold value $Q_{TH}$ according to the blood volume of the observation target. This is because the distance between isolines of oxygen saturation in the correlation changes according to the signal ratio R2/G2 (refer to FIG. 9). For example, even if the signal ratio G2/B2 reflecting the amount of yellow dye is a fixed value, when the signal ratio R2/G2 is small and the blood volume is small, the distance between isolines of oxygen saturation is small. Even if the signal ratio G2/B2 deviates slightly, the error of the oxygen saturation calculated is large. Therefore, if the threshold value $Q_{TH}$ is changed according to the blood volume, it is possible to appropriately determine the magnitude of the influence of the amount of yellow dye on the calculation of oxygen saturation and give a warning for prompting the cleaning.

Figure 15:
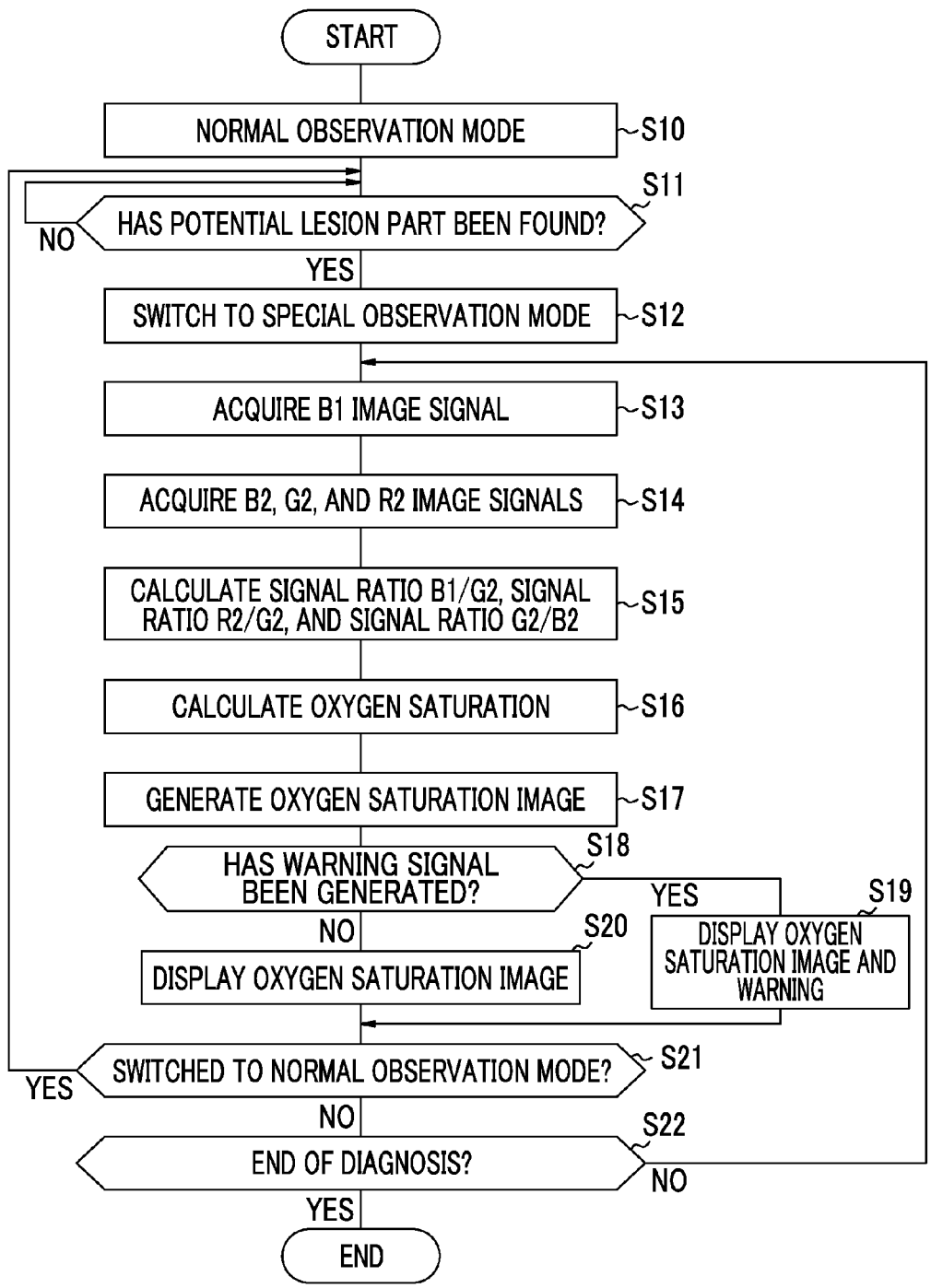
FIG. 15 is a flowchart showing the operation of the endoscope system.

Next, the flow of observation using the endoscope system 10 according to the present embodiment will be described with reference to the flowchart in FIG. 15. First, in the normal observation mode, screening is performed from the most distant view state (S10). In the normal observation mode, a normal observation image is displayed on the monitor 18. When a part that is likely to be a lesion (hereinafter, referred to as a potential lesion part), such as a brownish area or rubor, is found in this screening (S11), the mode selector SW 22b is operated for switching to the special observation mode (S12). Then, in the special observation mode, the potential lesion part is diagnosed.

In the special observation mode, the blue narrowband light and the white light are alternately emitted to the observation target in synchronization with the imaging frame of the sensor 48. Accordingly, the sensor 48 outputs the B1 image signal in the first frame, and outputs the R2 image signal, the G2 image signal, and the B2 image signal in the second frame. Then, in the processor device 16, when these imaging signals are acquired by the image signal acquisition unit 54 (S13 and S14: image signal acquisition step), the signal ratio calculation section 81 calculates the signal ratio B1/G2, the signal ratio R2/G2, and the signal ratio G2/B2 (S15: signal ratio calculation step). Based on the signal ratio B1/G2 and the signal ratio R2/G2 of these signal ratios, the oxygen saturation calculation section 83 calculates the oxygen saturation for each pixel (S16: oxygen saturation calculation step). Then, the image generation section 84 generates an oxygen saturation image based on the image signals B2, G2, and R2 and the oxygen saturation calculated by the oxygen saturation calculation section 83 (S17: oxygen saturation image generation step).

After the signal ratios are calculated by the signal ratio calculation section 81, the warning notification unit 65 acquires the signal ratio G2/B2 from the signal ratio calculation section 81, and compares the signal ratio G2/B2 with the threshold value $Q_{TH}$. As a result, when there is a pixel having the signal ratio G2/B2 equal to or greater than the threshold value $Q_{TH}$, the warning notification unit 65 generates a warning signal (S18 (warning signal generation step): YES). When the warning signal is received, the display image signal generation unit 66 prompts the cleaning of the observation target by displaying a warning message on the monitor 18 together with an oxygen saturation image (S19). On the other hand, when there is no pixel having the signal ratio G2/B2 equal to or greater than the threshold value $Q_{TH}$, no warning signal is generated (S18:NO), and the display image signal generation unit 66 displays an oxygen saturation image on the monitor 18 (S20).

In addition, these operations are repeatedly performed until the switching to the normal observation mode (S21) or until the end of diagnosis (S22).

As described above, the endoscope system 10 determines whether or not the observation target is very contaminated with mucus containing yellow dye or the like by comparing the signal ratio G2/B2 with the threshold value $Q_{TH}$, and displays the warning message 102 on the monitor 18 to prompt the cleaning of the observation target when there is a severe amount of dirt causing a large error in the oxygen saturation. Thus, by displaying the warning message 102 to notify of the need for cleaning, a doctor who uses the endoscope system 10 can accurately grasp the severity of dirt adhering to the observation target when performing diagnosis based on the oxygen saturation of the observation target. In addition, when the warning message 102 is displayed, it is possible to perform diagnosis based on the oxygen saturation calculated after cleaning the observation target. Therefore, more accurate diagnosis can be performed.

In particular, the warning notification unit 65 changes the threshold value $Q_{TH}$ for comparison with the signal ratio G2/B2 according to the signal ratio R2/G2 (that is, the blood volume). Therefore, in the endoscope system 10, it is possible to appropriately determine the magnitude of the influence of the amount of yellow dye on the calculation of oxygen saturation and give a warning for prompting the cleaning.

The warning notification unit 65 may acquire the signal ratio B1/G2 from the signal ratio calculation section 81, and change the threshold value $Q_{TH}$ according to the signal ratio B1/G2. If the threshold value $Q_{TH}$ is changed according to the signal ratio B1/G2 as described above, the dependence of the threshold value $Q_{TH}$ on the oxygen saturation can be reduced. Therefore, compared with a case where the fixed threshold value $Q_{TH}$ is used, it is possible to appropriately determine the magnitude of the influence of the amount of yellow dye on the calculation of oxygen saturation and give a warning for prompting the cleaning. In addition, if the warning notification unit 65 is made to acquire the signal ratio R2/G2 and the signal ratio B1/G2 from the signal ratio calculation section 81 and change the threshold value $Q_{TH}$ according to these signal ratios, it is possible to reduce the dependence of the threshold value $Q_{TH}$ on the blood volume and the oxygen saturation. Therefore, it is possible to appropriately determine the magnitude of the influence of the amount of yellow dye on the calculation of oxygen saturation and give a warning for prompting the cleaning.

In the endoscope system 10, the warning message 102 is displayed on the monitor 18. Instead, it is also possible to prompt the cleaning of the observation target by outputting a warning sound, reproducing a warning message by voice, or turning on a lamp or a rotation lamp.

Figure 16:
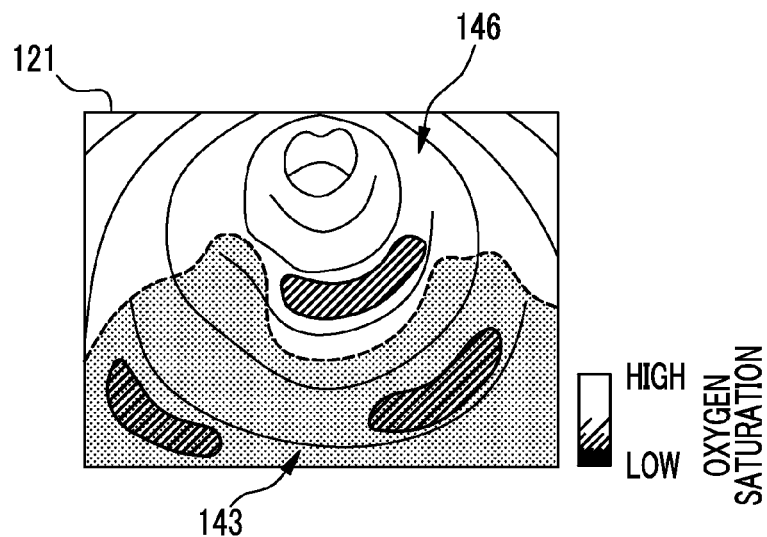
FIG. 16 is an explanatory view showing the operation in a modification example.

The warning notification unit 65 may detect a region where there is a pixel having the signal ratio G2/B2 equal to or greater than the threshold value $Q_{TH}$ and output a warning signal as position information of the pixel having the signal ratio G2/B2 equal to or greater than the threshold value $Q_{TH}$. In this case, for example, when converting the oxygen saturation image that is RGB image data into the brightness signal Y and the color difference signals Cb and Cr for display on the monitor 18, the display image signal generation unit 66 replaces the color difference signals Cb and Cr of the pixel having the signal ratio G2/B2 equal to or greater than the threshold value $Q_{TH}$ with zero. As a result, for example, as shown in FIG. 16, an oxygen saturation image 121 is displayed on the monitor 18. The oxygen saturation image 121 is divided into a contaminated region 143 where the signal ratio G2/B2 is equal to or greater than the threshold value $Q_{TH}$ and a clean region 146 where the signal ratio G2/B2 is less than the threshold value $Q_{TH}$. In the oxygen saturation image 121, the contaminated region 143 is displayed in an achromatic color, and the clean region 146 is displayed in a chromatic color that is pseudo-colored according to the oxygen saturation. Thus, by displaying differently a pixel having the signal ratio G2/B2 in a specific range and a pixel having the signal ratio G2/B2 outside the specific range, it is possible to visually determine a region where the error of oxygen saturation is large due to mucus containing yellow dye or the like. By observing the position or area of the contaminated region 143, it is possible to determine the need for cleaning. This replaces the warning message 102.

In this example, the color difference signals Cb and Cr of all pixels having the signal ratio G2/B2 equal to or greater than the threshold value $Q_{TH}$ are replaced with zero. However, the color difference signals Cb and Cr of only a pixel that has the signal ratio G2/B2 equal to or greater than the threshold value $Q_{TH}$ and has a pseudo-colored value (for example, less than 60%) of oxygen saturation may be replaced with zero so that the pixel is displayed in an achromatic color. In addition, although color adjustment is performed in a stage of generating the display image signal, the display color of the pixel having the signal ratio G2/B2 equal to or greater than the threshold value $Q_{TH}$ may be changed in a stage of generating the oxygen saturation image. In this case, the image generation section 84 performs this processing in response to a warning signal.

The pixel having the signal ratio G2/B2 equal to or greater than the threshold value $Q_{TH}$ may be displayed in a specific color by replacing the color difference signals Cb and Cr of the pixel having the signal ratio G2/B2 equal to or greater than the threshold value $Q_{TH}$ with a specific value set in advance, instead of replacing the color difference signals Cb and Cr of the pixel having the signal ratio G2/B2 equal to or greater than the threshold value $Q_{TH}$ with zero. In this case, it is preferable to select a color that will not be confused with a color used to display the oxygen saturation.

Figure 9:
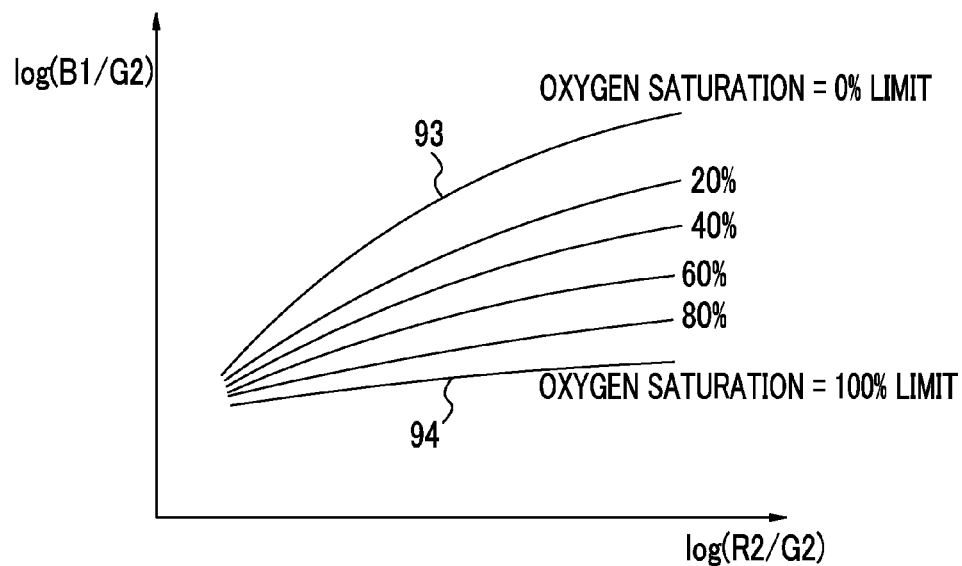
FIG. 9 is an explanatory diagram showing the correlation between a signal ratio and oxygen saturation.

Although the center wavelength of the B color filter is 450 nm in the present embodiment, this is a wavelength of an isosbestic point at which the absorption coefficient of oxygenated hemoglobin is almost equal to the absorption coefficient of reduced hemoglobin (refer to FIG. 9). Thus, by setting the center wavelength of light transmitted through the B color filter to a wavelength of the isosbestic point or a wavelength near the isosbestic point, it is possible to obtain the B2 image signal with low dependence on oxygen saturation. By using the B2 image signal corresponding to the wavelength band near the isosbestic point, it is possible to give a warning based on the presence of yellow dye or the concentration of yellow dye more accurately regardless of oxygen saturation.

The invention is particularly suitable for an endoscope system and an endoscope system processor device to calculate the oxygen saturation since a calculation error is likely to occur due to the presence of yellow dye. However, even when the invention is applied to an endoscope system and an endoscope system processor device that do not calculate the oxygen saturation, it is possible to objectively notify of the degree of contamination due to mucus containing yellow dye or the like. Therefore, the invention is suitable for the endoscope system and the endoscope system processor device that do not calculate the oxygen saturation.

In the embodiment described above, the broadband light source 36 is used. Instead of the broadband light source 36, it is also possible to use a light source that generates white light with LEDs of RGB or a light source that generates white light with a laser diode (LD) and a phosphor that is excited by laser light emitted from the LD and emits light. In the case of using these light sources, the rotary filter 37 may be used together as in the embodiments described above, or the wavelength band of illumination light or the amount of illumination light may be adjusted by ON/OFF of the LEDs or the LD or by distribution adjustment of the amount of light instead of the rotary filter 37.

Figure 17:
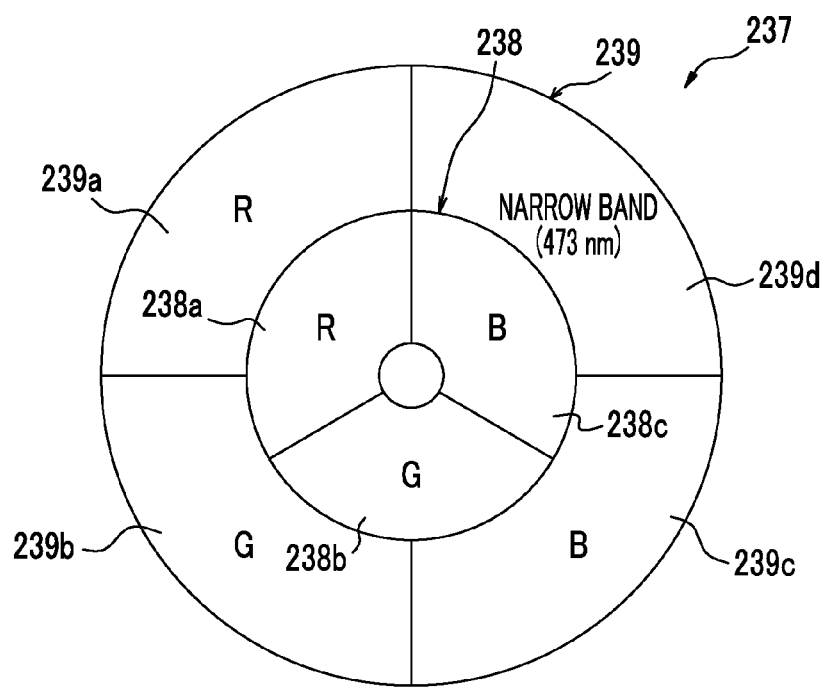
FIG. 17 is a rotary filter used in the case of using a monochrome imaging device.

Although the color imaging device in which RGB color filters are provided is used as the sensor 48 in the embodiment described above, a monochrome imaging device in which no color filter is provided may be used as the sensor 48. In this case, a rotary filter 237 shown in FIG. 17 is used.

The rotary filter 237 includes a normal observation mode filter 238 and a special observation mode filter 239, and is provided so as to be movable between a first position to place the normal observation mode filter 238 on the optical path of the white light and a second position to place the special observation mode filter 239 on the optical path of the white light. The normal observation mode filter 238 is provided in the inner peripheral portion of the rotary filter 237, and includes an R filter 238a that transmits red light, a G filter 238b that transmits green light, and a B filter 238c that transmits blue light. Therefore, when the rotary filter 237 is placed at the first position for normal light observation mode, the white light from the broadband light source 36 is incident on one of the R filter 238a, the G filter 238b, and the B filter 238c according to the rotation of the rotary filter 237. As a result, red light, green light, and blue light are sequentially emitted to the observation target according to the transmitted filter, and the monochrome sensor outputs sequentially an R image signal, a G image signal, and a B image signal by imaging the observation target with reflected light of the red light, the green light, and the blue light.

The special observation mode filter 239 is provided in the outer peripheral portion of the rotary filter 237. The special observation mode filter 239 includes an R filter 239a that transmits red light, a G filter 239b that transmits green light, a B filter 239c that transmits blue light, and a narrowband filter 239d that transmits narrowband light of 473±10 nm. Therefore, when the rotary filter 237 is placed at the second position for special observation mode, the white light from the broadband light source 36 is incident on one of the R filter 239a, the G filter 239b, the B filter 239c, and the narrowband filter 239d according to the rotation of the rotary filter 237. As a result, red light, green light, blue light, and narrowband light (473 nm) are sequentially emitted to the observation target according to the transmitted filter, and the monochrome sensor outputs sequentially an R image signal, a G image signal, a B image signal, and a narrowband image signal by imaging the observation target with reflected light of the red light, the green light, the blue light, and the narrowband light.

RGB image signals acquired in the special observation mode correspond to the R2 image signal, the G2 image signal, and the B2 image signal in the first embodiment, respectively. The narrowband image signal acquired in the special observation mode corresponds to the B1 image signal in the first embodiment. Accordingly, subsequent processing can be performed in the same manner as in the endoscope system 10 according to the first embodiment.

Although the oxygen saturation is calculated based on the signal ratio B1/G2 and the signal ratio R2/G2 in the embodiment described above, it is also possible to calculate the oxygen saturation based on only the signal ratio B1/G2. In this case, it is preferable to store the correlation between the signal ratio B1/G2 and the oxygen saturation in the correlation storage section 82.

Although the oxygen saturation image obtained by imaging the oxygen saturation is generated and displayed in the embodiment described above, a blood volume image obtained by imaging the blood volume may be generated and displayed in addition to the generation and display of the oxygen saturation image. Since the blood volume is correlated with the signal ratio R2/G2, a blood volume image obtained by imaging the blood volume can be generated by assigning different colors according to the signal ratio R2/G2.

In the embodiments described above, the oxygen saturation is calculated. However, instead of or in addition to the oxygen saturation, other biological function information, such as an oxygenated hemoglobin index that is calculated from "blood volume×oxygen saturation (%)" or a reduced hemoglobin index that is calculated from "blood volume× (1−oxygen saturation) (%)", may be calculated.

Figure 18:
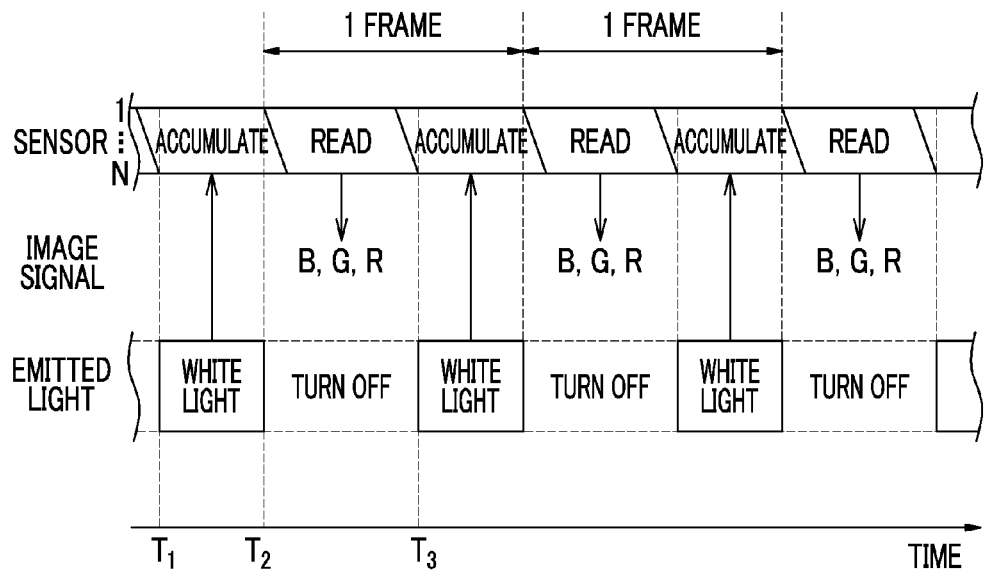
FIG. 18 is an explanatory view showing imaging control in the normal observation mode in the case of using a CMOS image sensor.
Figure 19:
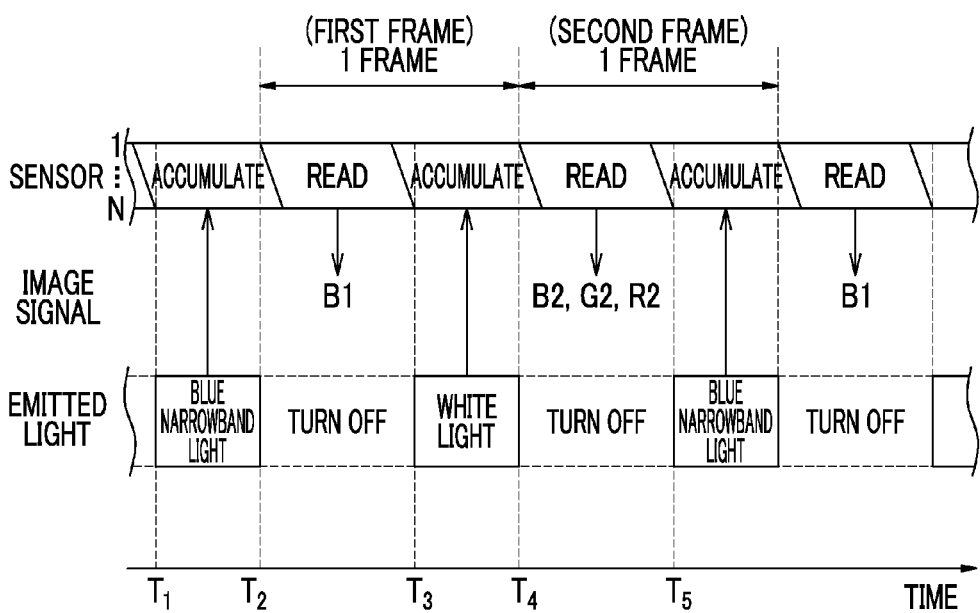
FIG. 19 is an explanatory view showing imaging control in the special observation mode in the case of using a CMOS image sensor.

Although the CCD image sensor is used as the sensor 48 in the embodiments described above, a CMOS image sensor may also be used as the sensor 48. In this case, the CMOS image sensor is driven in a so-called rolling shutter method, and accumulation and reading of the signal charge are sequentially performed for each row (each of first to N-th rows) of pixels. For this reason, the timing of the accumulation and reading of the signal charge of each row differs according to each row. Therefore, switching between the blue narrowband light (or the green narrowband light) and the white light is preferably performed in accordance with the reading timing. For example, as shown in FIG. 18, in the normal observation mode, the emission of the white light is performed until the accumulation of the first row is completed (time $T_2$) from the start of the accumulation of the N-th row (time $T_1$), while the emission of the white light is stopped until the reading of the N-th row is completed (time $T_3$) from the start of the reading of the first row (time $T_2$). In addition, as shown in FIG. 19, in the special observation mode, the emission of the blue narrowband light is performed until the accumulation of the first row is completed (time $T_2$) from the start of the accumulation of the N-th row (time $T_1$), while the emission of the blue narrowband light and the white light is stopped until the reading of the N-th row is completed (time $T_3$) from the start of the reading of the first row (time $T_2$). Then, in the next frame, the emission of the white light is performed until the accumulation of the first row is completed (time $T_4$) from the start of the accumulation of the N-th row (time $T_3$), while the emission of the blue narrowband light and the white light is stopped until the reading of the N-th row is completed (time $T_5$) from the start of the reading of the first row (time $T_4$). Thus, it is possible to standardize the length (exposure) of the substantial charge accumulation period of each row and to prevent the signal based on the blue narrowband light and the signal based on the white light from being mixed. Therefore, even when a CMOS image sensor is used as the sensor 48, it is possible to calculate an accurate oxygen saturation as in the embodiments described above.

What is claimed is:

1. An endoscope system, comprising:
 a processor device configured to
 acquire a first image signal corresponding to a first wavelength range where an amount of light absorption changes according to concentration of yellow dye, a second image signal corresponding to a second wavelength range where the amount of light absorption changes according to a blood volume of an observation target, and a third image signal corresponding to a third wavelength range where a change in the amount of light absorption according to the concentration of the yellow dye is small compared with the first wavelength range and a change in the amount of light absorption according to the blood volume is small compared with the second wavelength range,
 calculate a first signal ratio for each pixel based on the first and second image signals and calculates a second signal ratio for each pixel based on the second and third image signals, and
 calculate a threshold value for comparison with the first signal ratio according to the second signal ratio and generate a warning signal for giving a warning for prompting cleaning of the observation target based on a comparison result between the first signal ratio and the threshold value.

2. The endoscope system according to claim 1,
 wherein the first signal ratio is a ratio of a pixel value of the second image signal to a pixel value of the first image signal.

3. The endoscope system according to claim 2,
 wherein the second signal ratio is a ratio of a pixel value of the third image signal to a pixel value of the second image signal.

4. The endoscope system according to claim 3,
 wherein the first wavelength range includes an isosbestic point at which the amount of light absorption with respect to the oxygen saturation of blood hemoglobin is fixed.

5. The endoscope system according to claim 2, further comprising:
 wherein the processor device acquires a fourth image signal corresponding to a fourth wavelength range where the amount of light absorption changes according to oxygen saturation of blood hemoglobin, and the processor device calculates the oxygen saturation of the observation target for each pixel based on at least the fourth image signal.

6. The endoscope system according to claim 2, wherein the first wavelength range includes an isosbestic point at which the amount of light absorption with respect to the oxygen saturation of blood hemoglobin is fixed.

7. The endoscope system according to claim 1, wherein the second signal ratio is a ratio of a pixel value of the third image signal to a pixel value of the second image signal.

8. The endoscope system according to claim 1, further comprising:
wherein the processor device acquires a fourth image signal corresponding to a fourth wavelength range where the amount of light absorption changes according to oxygen saturation of blood hemoglobin, and
the processor device calculates the oxygen saturation of the observation target for each pixel based on at least the fourth image signal.

9. The endoscope system according to claim 8, wherein the processor device calculates a third signal ratio for each pixel based on the second and fourth image signals, and
the processor device calculates the threshold value for comparison with the first signal ratio according to the second and third signal ratios.

10. The endoscope system according to claim 9, wherein the third signal ratio is a ratio of a pixel value of the fourth image signal to a pixel value of the second image signal.

11. The endoscope system according to claim 10, the processor device further configured to
an oxygen saturation image showing the oxygen saturation of the observation target, and
generate a display image signal for displaying the oxygen saturation image on a display,
wherein the warning signal includes a comparison result between the signal ratio of each pixel and the threshold value, and
the processor device makes a display in a pixel where the third signal ratio is within a specific range set in advance and a display in a pixel where the third signal ratio is outside the specific range different from each other based on the warning signal.

12. The endoscope system according to claim 9, the processor device further configured to:
generate an oxygen saturation image showing the oxygen saturation of the observation target, and
a generate a display image signal for displaying the oxygen saturation image on a display,
wherein the warning signal includes a comparison result between the signal ratio of each pixel and the threshold value, and
the processor device makes a display in a pixel where the third signal ratio is within a specific range set in advance and a display in a pixel where the third signal ratio is outside the specific range different from each other based on the warning signal.

13. The endoscope system according to claim 8, the processor device further configured to:
generate an oxygen saturation image showing the oxygen saturation of the observation target, and
generate a display image signal for displaying the oxygen saturation image on a display,
wherein the warning signal includes a comparison result between the signal ratio of each pixel and the threshold value, and
the processor device makes a display in a pixel where the third signal ratio is within a specific range set in advance and a display in a pixel where the third signal ratio is outside the specific range different from each other based on the warning signal.

14. The endoscope system according to claim 13, wherein the processor device generates the oxygen saturation image in which a color difference signal of the pixel where the third signal ratio is within the specific range is set to zero and a color difference signal of the pixel where the third signal ratio is outside the specific range is set to a value corresponding to the oxygen saturation.

15. The endoscope system according to claim 7, further comprising:
wherein the processor device acquires a fourth image signal corresponding to a fourth wavelength range where the amount of light absorption changes according to oxygen saturation of blood hemoglobin, and
the processor device calculates the oxygen saturation of the observation target for each pixel based on at least the fourth image signal.

16. The endoscope system according to claim 7, wherein the first wavelength range includes an isosbestic point at which the amount of light absorption with respect to the oxygen saturation of blood hemoglobin is fixed.

17. The endoscope system according to claim 1, wherein the first wavelength range includes an isosbestic point at which the amount of light absorption with respect to the oxygen saturation of blood hemoglobin is fixed.

18. An endoscope system processor device for an endoscope system, comprising:
a processor device configured to
acquire a first image signal corresponding to a first wavelength range where an amount of light absorption changes according to concentration of yellow dye, a second image signal corresponding to a second wavelength range where the amount of light absorption changes according to a blood volume of an observation target, and a third image signal corresponding to a third wavelength range where a change in the amount of light absorption according to the concentration of the yellow dye is small compared with the first wavelength range and a change in the amount of light absorption according to the blood volume is small compared with the second wavelength range,
calculate a first signal ratio for each pixel based on the first and second image signals and calculates a second signal ratio for each pixel based on the second and third image signals, and
calculate a threshold value for comparison with the first signal ratio according to the second signal ratio and generate a warning signal for giving a warning for prompting cleaning of the observation target based on a comparison result between the first signal ratio and the threshold value.

19. An operation method for an endoscope system, comprising:
a step of acquiring a first image signal corresponding to a first wavelength range where an amount of light absorption changes according to concentration of yellow dye, a second image signal corresponding to a second wavelength range where the amount of light absorption changes according to a blood volume of an observation target, and a third image signal corresponding to a third wavelength range where a change in the amount of light absorption according to the concentration of the yellow dye is small compared with the first wavelength range and a change in the amount of light absorption according to the blood volume is small compared with the second wavelength range using a processor device;

a step of calculating a first signal ratio for each pixel based on the first and second image signals and calculating a second signal ratio for each pixel based on the second and third image signals using the processor device; and a step of calculating a threshold value for comparison with the first signal ratio according to the second signal ratio and generating a warning signal for giving a warning for prompting cleaning of the observation target based on a comparison result between the first signal ratio and the threshold value using the processor device.

20. An operation method for an endoscope system processor device, comprising:

a step of acquiring a first image signal corresponding to a first wavelength range where an amount of light absorption changes according to concentration of yellow dye, a second image signal corresponding to a second wavelength range where the amount of light absorption changes according to a blood volume of an observation target, and a third image signal corresponding to a third wavelength range where a change in the amount of light absorption according to the concentration of the yellow dye is small compared with the first wavelength range and a change in the amount of light absorption according to the blood volume is small compared with the second wavelength range using a processor device;

a step of calculating a first signal ratio for each pixel based on the first and second image signals and calculating a second signal ratio for each pixel based on the second and third image signals using the processor device; and a step of calculating a threshold value for comparison with the first signal ratio according to the second signal ratio and generating a warning signal for giving a warning for prompting cleaning of the observation target based on a comparison result between the first signal ratio and the threshold value using the processor device.

* * * * *